United States Patent
Kiez

(10) Patent No.: US 10,245,202 B2
(45) Date of Patent: Apr. 2, 2019

(54) TEMPORARY MORGUE SYSTEM

(71) Applicant: Chris Kiez, Carp (CA)

(72) Inventor: Chris Kiez, Carp (CA)

( * ) Notice: Subject to any disclaimer, the term of this patent is extended or adjusted under 35 U.S.C. 154(b) by 240 days.

(21) Appl. No.: 15/278,789

(22) Filed: Sep. 28, 2016

(65) Prior Publication Data
US 2018/0049429 A1 Feb. 22, 2018

(51) Int. Cl.
*A61G 17/00* (2006.01)
*A01N 1/00* (2006.01)

(52) U.S. Cl.
CPC ............ *A61G 17/002* (2013.01); *A01N 1/00* (2013.01); *A61G 17/00* (2013.01)

(58) Field of Classification Search
CPC ...... A01N 1/00; A61G 17/044; A61G 17/002; A61G 19/00; A61G 21/00; A61G 17/00; E04H 13/00; E04H 1/12; E04B 1/343
USPC ...................... 27/11, 35, 1, 2; 296/24.35, 20
See application file for complete search history.

(56) References Cited

U.S. PATENT DOCUMENTS

| | | | | |
|---|---|---|---|---|
| 4,723,418 A * | 2/1988 | Whitmer, II | ......... | A61G 17/002 62/298 |
| 4,773,230 A * | 9/1988 | Garrett | ..................... | A01N 1/00 27/11 |
| 4,879,789 A * | 11/1989 | Bak | .......................... | A01N 1/00 27/11 |
| 5,715,583 A * | 2/1998 | Sandoval | ................ | A01N 1/00 27/11 |
| 5,924,181 A * | 7/1999 | Takasugi | .............. | A61G 17/002 27/11 |
| 6,299,229 B1 * | 10/2001 | Becenas Nieto | ...... | A61G 21/00 296/24.3 |
| 8,291,648 B1 * | 10/2012 | Orr | ..................... | E04B 1/34305 52/86 |
| 2008/0256767 A1 * | 10/2008 | Berns | .................... | E04B 1/3444 27/35 |
| 2008/0307822 A1 * | 12/2008 | Richardson | .......... | A61G 17/002 62/376 |
| 2010/0052351 A1 * | 3/2010 | Sartin | ..................... | B60P 1/431 296/20 |

* cited by examiner

*Primary Examiner* — William L Miller
(74) *Attorney, Agent, or Firm* — Loza & Loza, LLP; Heidi L. Eisenhut

(57) ABSTRACT

In at least one embodiment the present invention provides a mobile storage system including a container having a first end, second end, first side, second side, ceiling and floor defining a rectangular prismatic cavity, an access door that corresponds with an access opening positioned on at least one of the longitudinal sides between the first end and the second end of the container, a climate control unit for cooling the container, a rack unit positioned within one of the first end and the second end of the container and adapted to slidably yet releasably receive a tray in a stowed position, and a mobile stretcher adjustable from a first height to a least a second height and adapted to securely yet releasably receive the tray.

19 Claims, 10 Drawing Sheets

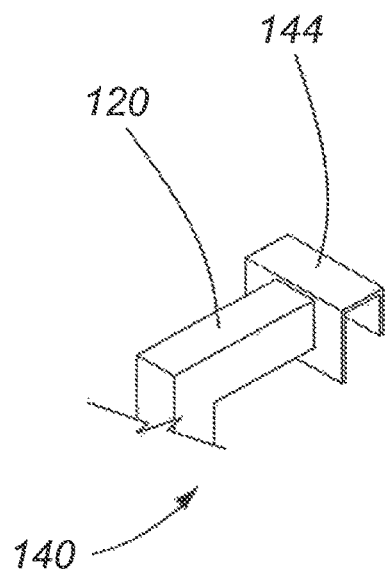
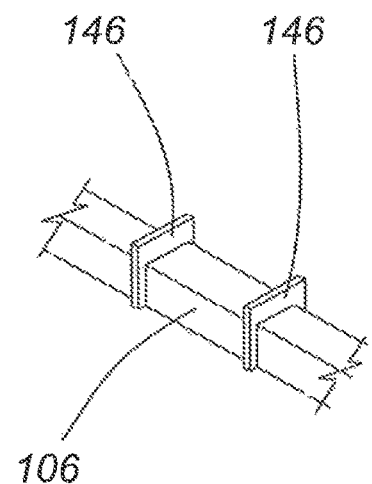
FIG. 7A  FIG. 7B
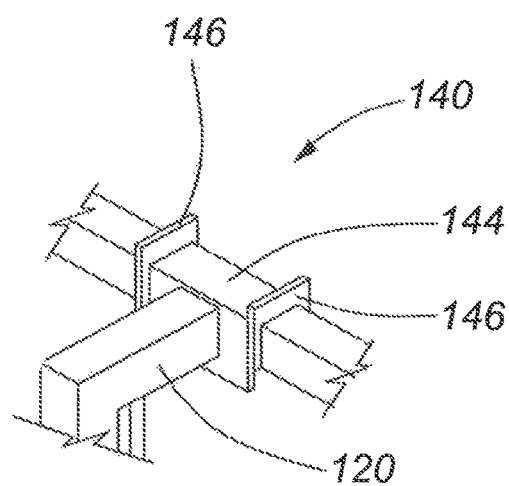
FIG. 7C

TEMPORARY MORGUE SYSTEM

FIELD

The present invention relates to disaster relief and emergency response infrastructure. More specifically, the present invention relates to a temporary, mobile mortuary system that requires limited preventative maintenance, is robust, and can be quickly deployed in the face of the significant logistical challenges presented by a natural disaster or a public emergency.

BACKGROUND

Unexpected natural disasters and public emergencies can significantly strain the resources of the first response teams that are tasked with coordinating a response to these traumatic events.

Accordingly, many local governments, police and fire departments and emergency health providers have predetermined and comprehensive emergency management plans in place which assign explicit roles to the various organizations and public authorities that are deployed in the event of a natural disaster or public emergency.

One of the many tasks that presented during disaster response is the collection, preservation and forensic identification of any cadavers or human remains. As one will readily appreciate, time becomes a critical factor when dealing with casualties and forensic science, as any delay can result in evidential spoliation and the possibility of introducing health hazards to the site. For example, if cadavers or human remains are not dealt with in a timely manner, infectious diseases can be transmitted that can exacerbate the severity of the event for any adjacent residents and first-responders. Additionally, decay can impede victim identification as DNA can be severely degraded when exposed to the elements as will be readily understood by the skilled person. As such, it is of critical importance to quickly collect and transport human remains from the disaster site to medical grade storage.

Another major challenge presented during a natural disaster is that municipal infrastructure (such as water treatment, electricity and transport arteries) regularly fails. It is contemplated that having an on-site yet mobile morgue can help first responders manage these infrastructure failures.

Moreover, most municipalities' mortuary capacity is quickly outpaced by the volume of cadavers and human remains that can unfortunately be generated by a mass casualty event. As such, a robust, easily-deployed and self-contained unit that can be delivered to the site of a mass casualty eases enormous strain on local storage resources, which can increase the pace of victim identifications and keep remains centrally stored for key evidentiary issues that accompany post-event inquiries.

Accordingly, facilities are required that can store cadavers and human remains in a secure and dignified manner. In some jurisdictions, it is required by law to maintain and have access to temporary morgue facilities.

Ideally, these facilities must be secure and can be deployed in any weather, require minimal upkeep and preventative maintenance when not in use and provide a space where professional responders can work with the deceased in a manner that is sufficiently organized and controlled to ensure that the necessary tasks can be completed quickly and efficiently.

Currently, there is a clear deficit of suitable solutions that address the concerns presented herein. In some situations, existing public buildings or spaces are used for housing a makeshift morgue, however, it will be readily appreciated that using public facilities for the storage and identification of cadavers and human remains presents a number of health and public-relations issues that are undesirable.

Similarly, it will be readily appreciated that repurposing equipment (such as a refrigerated storage locker of transport trailer) for the purposes of storing human cadavers or remains is undesirable given the opportunities for cross-contamination and the general aesthetic concerns that are fundamentally present when dealing with matters of this nature.

Moreover, tent-based systems have been used in mass-fatality events that include a tent structure for temporarily housing a number of stretchers/gurneys, racking/shelving systems, examination tables and any other suitable mortuary equipment for quick deployment in the event of a mass-fatality event. Such tent-based systems are truly temporary and can be surprisingly expensive given their fragility and functional limitations, cannot be transported with cadavers or human remains inside and do not provide a secure storage space in the event that a secondary event (aftershock, terrorist attack, etc.) were to occur. Further, tent-based systems are soft-sided which makes temperature control difficult if not impossible and require a significant degree of set-up and as such do not offer optimal ease of deployment.

Moreover, trailer-based temporary morgue systems are also well-known and are relatively easy to deploy, however, these systems tend to be quite expensive given the specialized equipment required. Also, currently available trailer-based systems present significant loading and unloading challenges given the layout of a standard tractor trailer, and can have considerable durability/lifespan issues.

Accordingly, there is need for a temporary morgue system that is highly mobile, secure, robust, easy to deploy, easy to load, affordable and easily climate-controlled.

BRIEF SUMMARY

It is contemplated that the present invention can provide a temporary morgue system that is highly mobile, secure, robust, easy to deploy, easy to load, affordable and easily climate-controlled.

In at least one embodiment, the present invention provides a mobile storage system having a container having a first end, second end, first side, second side, ceiling and floor defining a rectangular prismatic cavity, an access door that corresponds with an access opening positioned on at least one of the longitudinal sides between the first end and the second end of the container, a climate control unit for controlling the climate within the container, a rack unit positioned within one of the first end and the second end of the container and adapted to slidably yet releasably receive a tray in a stowed position, and, in some embodiments, a mobile stretcher adjustable from a first height to a least a second height and adapted to securely yet releasably receive the tray.

More specifically, in at least one embodiment the present invention provides a mobile storage system including a container, the container having a first end having an internal supporting rear wall, a second end having an internal supporting rear wall, a first longitudinally extending side extending between the first end and the second end and having an internal supporting side wall, a second longitudinally extending side extending between the first end and the second end and having an internal supporting side wall, a supporting floor extending between the first end and the second end, a ceiling extending between the first end and the second end, the first end, the second end, the first longitudinally extending side, the second longitudinally extending side, the ceiling and the supporting floor defining a rectangular prismatic cavity, at least one of the first longitudinally extending side and the second longitudinally extending side having an access door that corresponds with an access opening, the access door and the access opening positioned between the first end and the second end of the container, and a climate control unit for controlling the climate within the container, at least one rack unit positioned within the rectangular prismatic cavity in at least one of the first end and the second end of the container, each at least one rack unit comprising, a front vertical first side support member having a first end and a second end and an inner surface and a front vertical second side support member having a first end and a second end and an inner surface, each of the front vertical first side support member and the front vertical second side support member having at least one tray support element positioned between the respective first end and the second end on the inner surface of the front vertical first side support member and the front vertical second side support member, a front upper lateral member having a first end and a second end and levelly extending between the front vertical first side support member and the front vertical second side support member adjacent the respective first end of each of the front vertical first side support member and the front vertical second side support member, a front lower lateral member having a first end and a second end and levelly extending between the front vertical first side support member and the front vertical second side support member adjacent the respective second end of each of the front vertical first side support member and the front vertical second side support member, a rear vertical first side support member having a first end and a second end and an inner surface and a rear vertical second side support member having a first end and a second end and an inner surface; each of the rear vertical first side support member and the rear vertical second side support member having at least one tray support element positioned between the respective first end and the second end on the inner surface of the rear vertical first side support member and the rear vertical second side support member, a rear upper lateral member having a first end and a second end and levelly extending between the rear vertical first side support member and the rear vertical second side support member adjacent the respective first end of each of the rear vertical first side support member and the rear vertical second side support member, a rear lower lateral member having a first end and a second end and levelly extending between the rear vertical first side support member and the rear vertical second side support member adjacent the respective second end of each of the rear vertical first side support member and the rear vertical second side support member, at least one tray having a first end, a second end, a first side and a second side, the at least one tray slidably supported by each at least one tray support element in a stowed position, and at least one vertical tray securing member having a first end and a second end, each at least one vertical tray securing member corresponding to at least one of the at least one tray; the at least one tray securing member abutting or nearly abutting the first end of the tray, the first end of the at least one vertical tray securing member removably engaging the front upper lateral member and the second end of the at least one vertical tray securing member removably engaging the front lower lateral member, and a mobile stretcher, the mobile stretcher adjustable from a first height to a least a second height and adapted to securely yet releasably receive the at least one tray, the at least a second height aligning with the at least one tray when it is supported by the at least one tray support element in a stowed position.

DESCRIPTION OF THE FIGURES

The present invention will be better understood in connection with the following Figures, in which:

FIGS. 7A to 7C are close-up isometric views of one embodiment of a retention bracket hook arrangement for use in connection with a rack unit of the mobile storage system of FIG. 1;

DETAILED DESCRIPTION OF THE EMBODIMENTS

Figure 1:
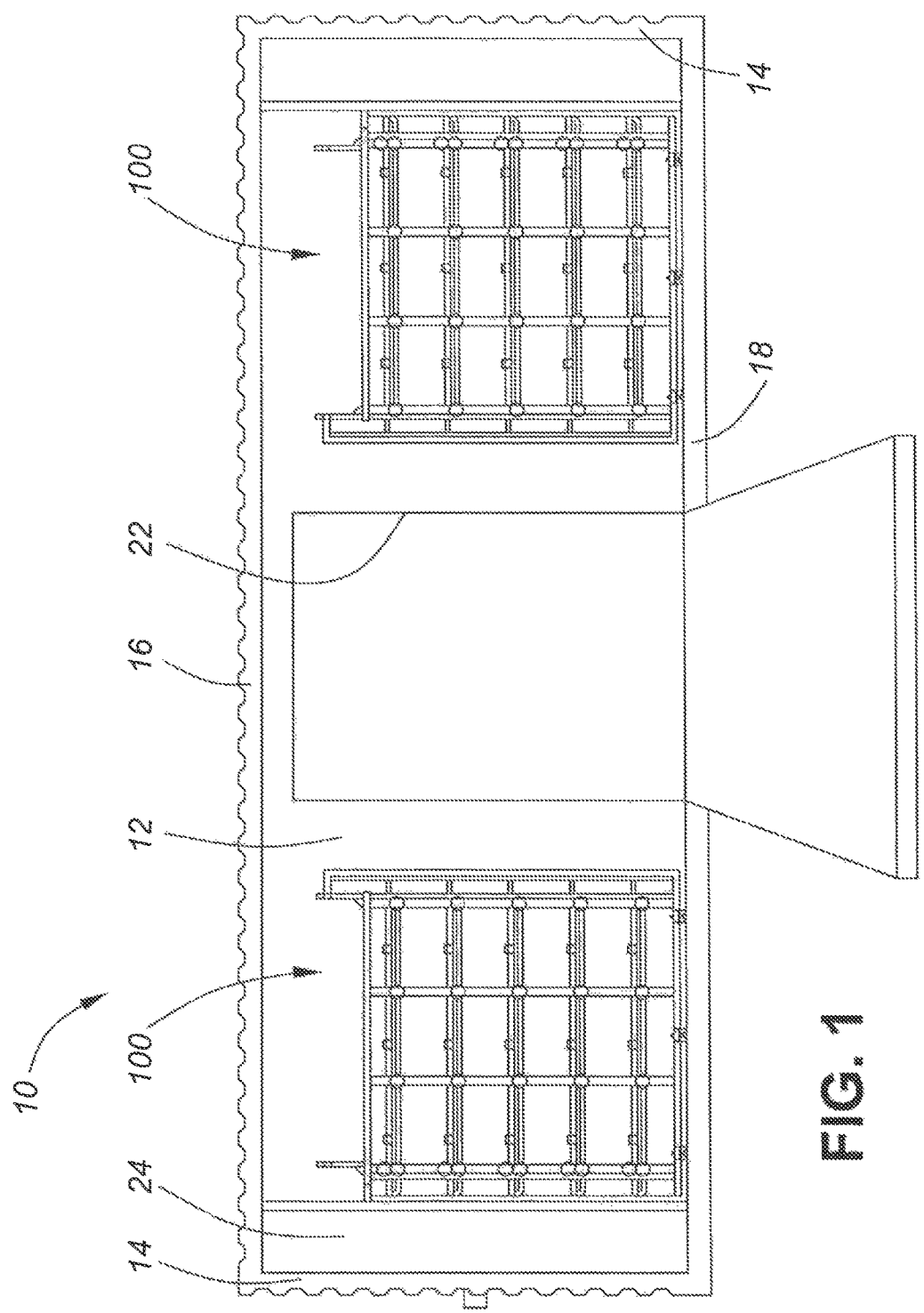
FIG. 1 is a side cutaway view of a mobile storage system in accordance with at least one embodiment of the present invention.

As discussed previously, it is contemplated that the present invention can provide a temporary morgue system that is highly mobile, secure, robust, easy to deploy, easy to load, affordable and easily climate-controlled.

As will be readily understood by the skilled person, it is contemplated that all of the components discussed herein can be formed by any suitable manufacturing process and can be formed of any suitable material that provides the requisite physical qualities as required by the particular end user application of the present invention. Moreover, all components can be formed in any size or dimensions as required by the particular end user application of the present invention.

All components discussed herein can be interconnected by any suitable means, including mechanical means (such as, but not limited to, rivets, machine screws and carriage bolts), welds, and adhesives, among any other suitable arrangements that will be readily appreciated by the skilled person. Moreover, it is contemplated that each component (or group of components) discussed herein can be formed of a single unitary component or a number of separate components suitable joined together as required by the particular end user application of the present invention.

In at least one embodiment, it is contemplated that the present invention can consist of a container unit, at least one rack unit and a stretcher.

It is contemplated that the present invention can employ a wide variety of container shapes and sizes as required by the particular end user application of the present invention. In at least one embodiment, it is contemplated that the present invention can employ a modified, refrigerated intermodal shipping container (also known as a sea can, cargo/freight container, ISO container, sea/ocean container, etc.) however other types of containers, both standardized and custom built, are also contemplated for use in connection with the present invention, including but not limited to a modified semi-trailer or a purpose built container, as required by the specific needs of the particular end user application.

In at least one embodiment, the container will have a first end, a second end, a longitudinally extending first side, a longitudinally extending second side, a supporting floor and a ceiling. In one embodiment, the first end, second end, longitudinally extending first side, longitudinally extending second side, supporting floor and ceiling collectively define an internal, rectangular prismatic cavity. In some embodiments, the first end or the second end could also function as doors (particularly where modified, pre-existing container are used), however these end-mounted doors are not contemplated as necessary for the proper functioning of the present invention.

As will be readily understood by the skilled person, the first end and the second end both include an internal supporting rear wall. Similarly, the first longitudinally extending side and the second longitudinally extending side both include an internal supporting side wall. As will be discussed in greater detail below, it is contemplated that additional components discussed herein will be mounted securely to the internal supporting end walls and/or the internal supporting side wall as the case may be. In some embodiments it is contemplated that a work table or folding work space can be mounted to one of the internal supporting end walls opposite the access opening, as will be readily understood by the skilled person.

It is contemplated that at least one, or both, of the first longitudinal side wall and the second longitudinal side wall include an access opening having a corresponding and cooperating access door. This access opening provides entry and egress into the internal cavity of the container.

In at least one embodiment, it is contemplated that the access opening and access door are positioned midway between the first end and the second end, however other arrangements are also contemplated. As discussed above, it is contemplated that the container can include either one or two access openings with one or two corresponding access doors as required by the particular end user application of the present invention. It is contemplated that the access door and access opening can take any suitable form, including but not limited to a sliding door, overhead door, an outwardly-swinging door, a roll-up door and an insulated door, among any other suitable type of door as will be readily appreciated by the skilled person, provided that a user of the present invention can readily access the interior of the container through the access opening.

It is also contemplated that the container can include a number of auxiliary systems including electrical power supply, a climate control unit, a cooling unit, a heating unit, electrical lighting systems and air filtration systems, among any other type of auxiliary systems that will be readily understood by the skilled person, as required by the particular end user application of the present invention.

In some embodiments, the container includes a portable and stowable ramp that is adapted to permit easy access to the access opening, as will be readily understood by the skilled person. In some embodiments, the container is equipped with a stowage space for the ramp, which can be accessed externally.

It is contemplated that the rack units can accommodate a single tray, or a number of trays, depending on the particular end user application of the present invention. In at least one embodiment, it is contemplated that each rack unit can have a first side that is positioned adjacent one side of the container and a second side that is positioned adjacent the other side of the container. It is also contemplated that the rear of the rack unit can abut the inner supporting rear wall of the end of the container.

It is also contemplated that the trays can be secured within the rack unit by any suitable means, including but not limited by way of a tray securing member as will be discussed in further detail below.

In these embodiments, each side of the rack unit can be comprised of a number of vertical support members that project upwardly from the floor of the container. Further, each side of the frame can have a lower horizontal member and an upper horizontal member that are connected by the vertical support members. In some embodiments, it is contemplated that at least one end of the horizontal member is fixed to the internal supporting wall of the end of the container by any suitable means. In some embodiments, it is also contemplated that the lower horizontal member can be affixed securely to the floor of the container by any suitable means.

It is further contemplated that the first side and the second side of the frame can be connected by way of front and rear upper lateral members and front and rear lower lateral members. Further, it is contemplated that at least one end of these lateral members can be fixed to the internal supporting side wall by any suitable means.

In some embodiments, it is contemplated that one or more partitions can be included in the rack system to separate multiple vertical rows of trays from one another in certain embodiments, as will be discussed in further detail below. It is contemplated that each partition can include a number of vertical support members that extend upwardly from the floor of the container. Moreover, the partition can include a lower horizontal member and an upper horizontal member that are connected by the vertical support members. In some embodiments, it is contemplated that at least one end of the horizontal member is fixed to the internal supporting rear wall of the end of the container by any suitable means, in an analogous fashion as discussed previously. In some embodiments, it is also contemplated that the lower horizontal member can be affixed securely to the floor of the container by any suitable means, in an analogous fashion as discussed previously.

It is further contemplated that the vertical support members can each include at least one tray support element that corresponds to at least one tray. In at least one embodiment, it is contemplated that these tray support elements are positioned along the sides of these vertical support members and are oriented such that a suitable number of tray support elements are mounted at the same height in opposing pairs on laterally adjacent vertical members such that they can support a tray that is adapted for holding a cadaver or human remains, as discussed in further detail below.

In at least one embodiment and as will be understood by the skilled person, it is contemplated that at least two opposing pairs (i.e. a minimum of four tray support elements total) of tray support elements are provided at the same height in order to support a corresponding tray, however it is contemplated that any suitable number of tray support elements may be employed.

It is further contemplated that in at least one embodiment the tray support element is a rotatable cylindrical component that permits easy loading and unloading of the trays in the rack system, as discussed in further detail below.

In at least one embodiment and as discussed above, it is contemplated that the rack system can be used to store at least one tray. This tray can take variety of forms and is adapted to secure a cadaver or human remains. In at least one embodiment it is contemplated that the tray is sized such that it can fit between the laterally adjacent vertical support members that form the first side of the rack unit and the second side of the rack unit. Moreover, in embodiments including partitions it is contemplated that the tray is sized to fit between laterally adjacent partitions, or between a partition and either side of the frame, as will be readily appreciated by the skilled person.

It is contemplated that in some embodiments the tray can include a lateral securing strap and can also have a laterally extending handle positioned at either end of the tray. In some embodiments, it is contemplated that the tray can have an upwardly concave depression that extends partially or fully across the surface of the tray, as will be readily appreciated by the skilled person.

In at least one embodiment, the rack system can also include a tray securing member that is movable and designed to keep the stowed trays secure, however other arrangements are also contemplated. In at least one embodiment, it is contemplated that the tray securing member can be a bar that abuts or nearly abuts one end of the tray when stowed within the rack system such that the tray will not be dislodged when the entire system is in transit.

In at least one embodiment, the tray securing member is a square "C" shaped component that releasably engages the front upper lateral member and the front lower lateral member of the rack unit. It is contemplated that one or both ends of the tray securing member can include a bracket retention hook adapted to engage the lateral members, among any other arrangement that will be readily appreciated by the skilled person. Moreover, it is contemplated that either end of the tray securing member can be temporarily secured in place by a fastener (such as, but not limited to a machine screw, carriage bolt, wing nut or eyebolt) that can be removed when access to the stowed trays is required.

Moreover, it is contemplated that the inner surface of the tray securing member can include at least one hook that corresponds and is aligned with at least one tray. In these embodiments, it is contemplated that the tray can have at least one laterally extending handle located at one of the end of the tray, such that the hook engages the handle when the tray is stowed and the tray securing element is secured in place. In this way, it is contemplated that the trays stowed within the rack system will not be dislodged when the entire system is in transit.

It is also contemplated that in some embodiments the rack unit can include a vertically oriented bumper that is affixed to the internal supporting rear wall of the container such that one end of the tray abuts this vertically oriented bumper when the tray is in the stowed position.

The stretcher can take a number of forms as required by the particular end user application of the present invention. In at least one embodiment it is contemplated that the stretcher is wheeled, and is operable from a first height to at least a second height. Moreover, it is contemplated that the stretcher can securely yet releasably receive the tray for transporting a cadaver or human remains from a disaster site into the present mobile storage system for secure storage.

It is at least one embodiment it is contemplated that the stretcher (and tray) is sized such that the stretcher and tray can be completely rotated within the container without contacting the longitudinally extending sides of the container or either rack unit. In this way, it is contemplated that a user of the present invention can manipulate the stretcher within the container in an unimpeded manner.

In at least one embodiment it is contemplated that the stretcher has a pneumatic height adjustment mechanism, however it is also contemplated that the height of the stretcher is manually adjustable and in other embodiments it is contemplated that the stretcher includes an electric or hydraulic height adjustment mechanism, among other arrangements that will be readily appreciated by the skilled person.

Figure 2:
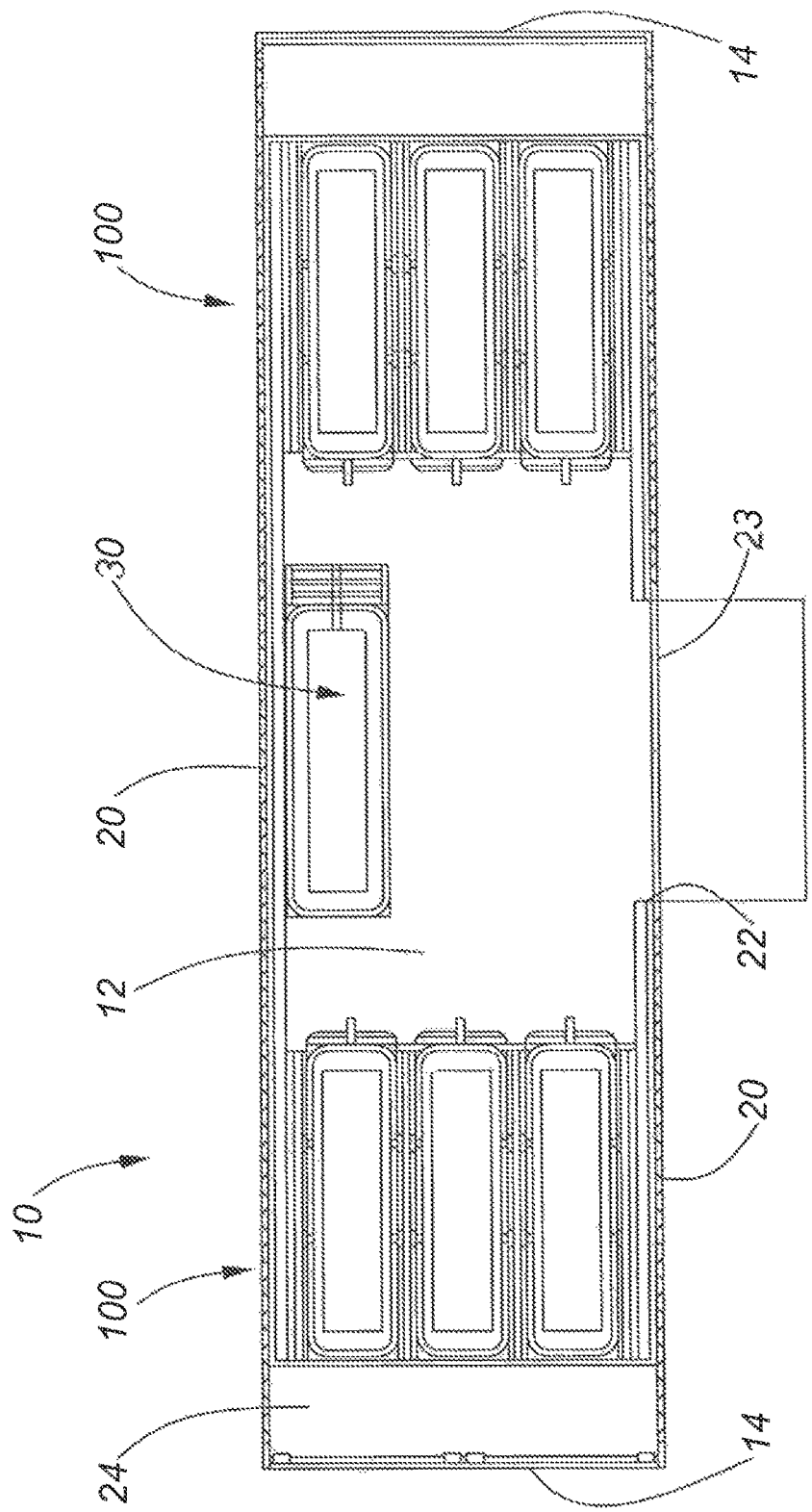
FIG. 2 is a top cutaway view of the mobile storage system of FIG. 1.

Turning to FIGS. 1 and 2, at least one embodiment of a mobile storage system in accordance with the present invention is illustrated. Mobile storage system 10 includes a container 12, two rack units 100 and a stretcher 30. Container 12 further includes a first end 14 and second end 14, a ceiling 16, a floor 18, a first longitudinally extending side 20 and second longitudinally extending side 20. An access opening 22 is provided in one of the longitudinally extending sides 20 approximately midway between first end 14 and second end 14, which cooperates with an access door 23. Further, an external ramp storage space 24 is included for stowing a ramp and any other critical supplies unique to establishing a disaster response site for the location, documentation and recovery of human remains (also known as, Disaster Victim Identification "DVI"), as will be readily understood by the skilled person.

Figure 3:
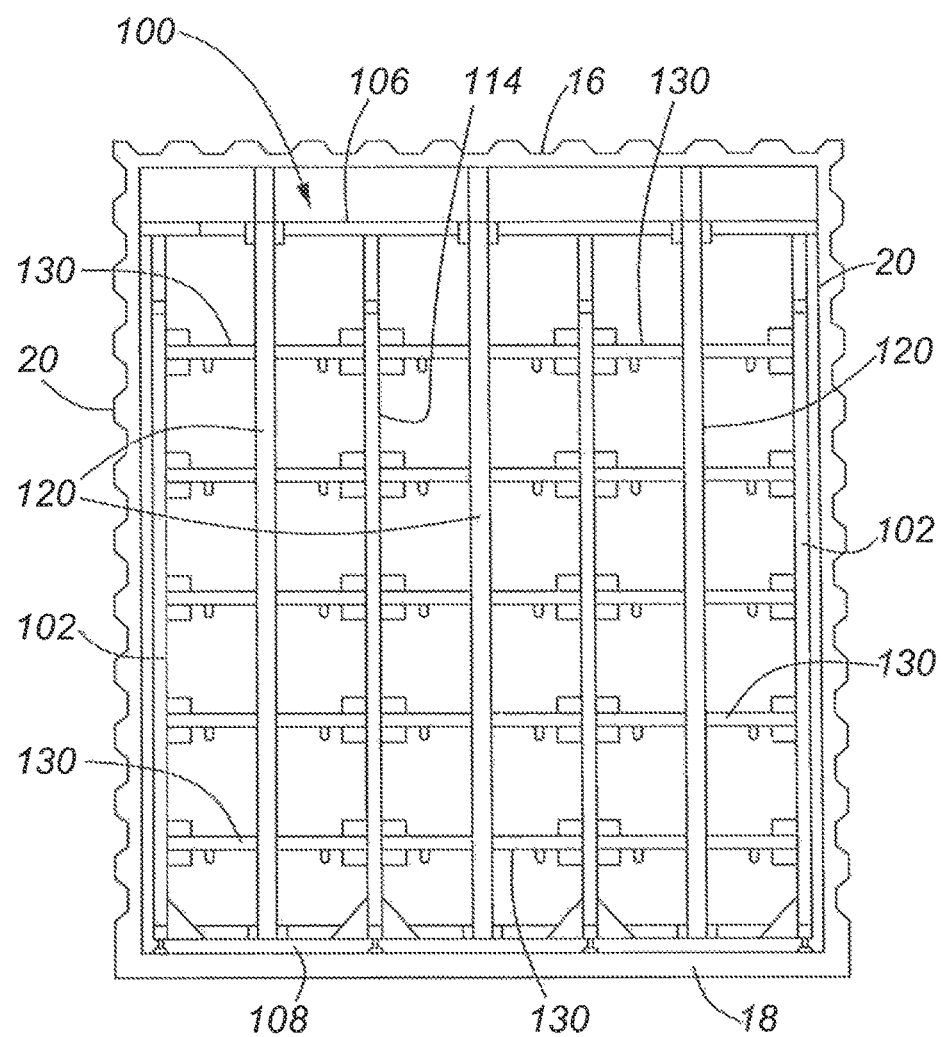
FIG. 3 is cutaway internal front end view of one embodiment of a rack unit for use in connection with the mobile storage system of FIG. 1.
Figure 4:
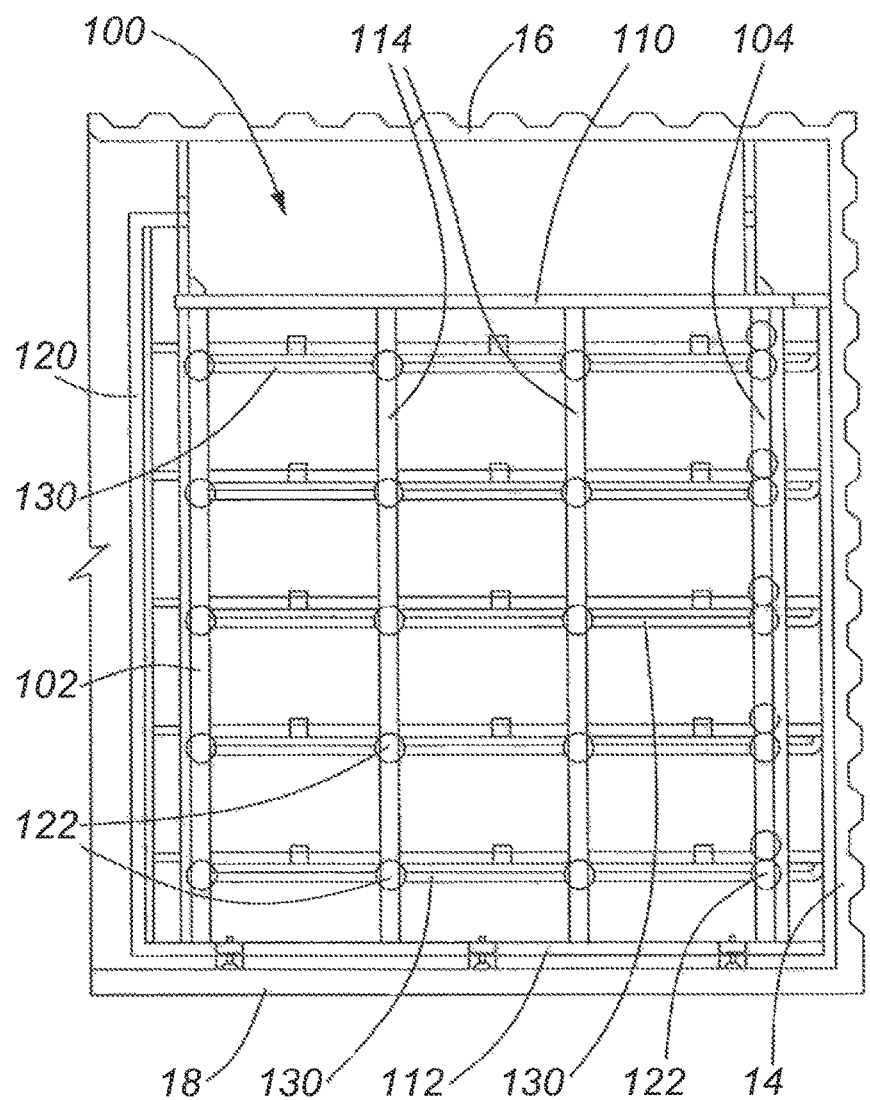
FIG. 4 is a side view of one embodiment of a rack unit for use in connection with the mobile storage system of FIG. 1.
Figure 5:
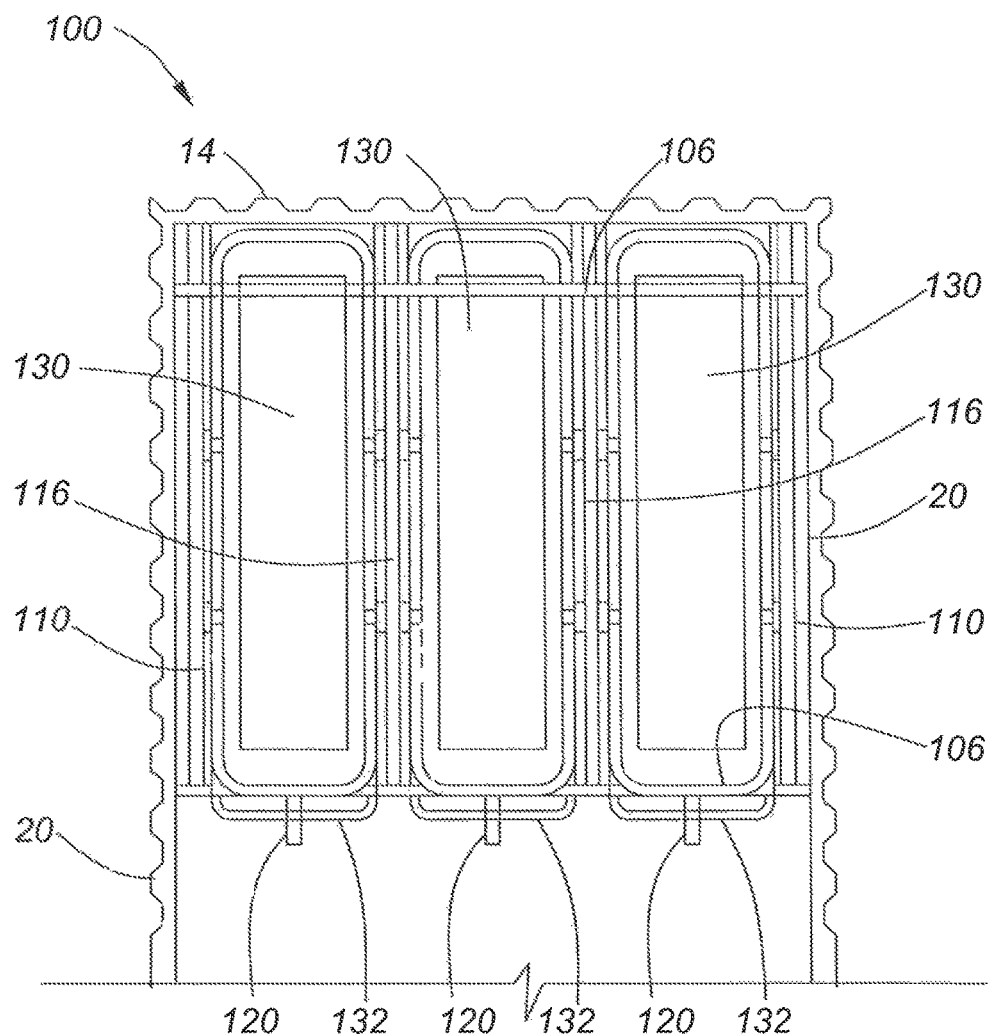
FIG. 5 is a top view of one embodiment of a rack unit for use in connection with the mobile storage system of FIG. 1.

Turning to FIGS. 3, 4 and 5, at least one embodiment of a rack unit in accordance with the present invention is illustrated. Rack unit 100 can include a front vertical first side support member 102 and front vertical second side support member 102, a rear vertical first side support member 104 and a rear vertical second side support member 104, a front upper lateral member 106 and a rear upper lateral member 106, a front lower lateral member 108 and rear lower lateral member 108, an upper first side horizontal member 110 and a upper second side horizontal member 110 and a lower first side horizontal member 112 and a lower second side horizontal member 112.

It is also contemplated that a number of vertical intermediary support members 114 and horizontal intermediary support members 116 can be included to form the partitions sections of the rack unit 100 as required. It is also contemplated that each side of the rack unit 100 can further include additional vertical intermediary support members 114.

It is contemplated that a number of tray securing elements 120 are also provided at the front end of rack unit 100, as will be discussed in further detail below.

It is contemplated that front vertical first side support member 102 and front vertical second side support member 102, rear vertical first side support member 104 and rear vertical second side support member 104 and vertical intermediary support members 114 can each include a number of tray support elements 122. In this embodiment, tray support element 122 is a cylindrical roller or a "stub" roller, however other arrangements are also contemplated as will be readily appreciated by the skilled person.

Figure 6:
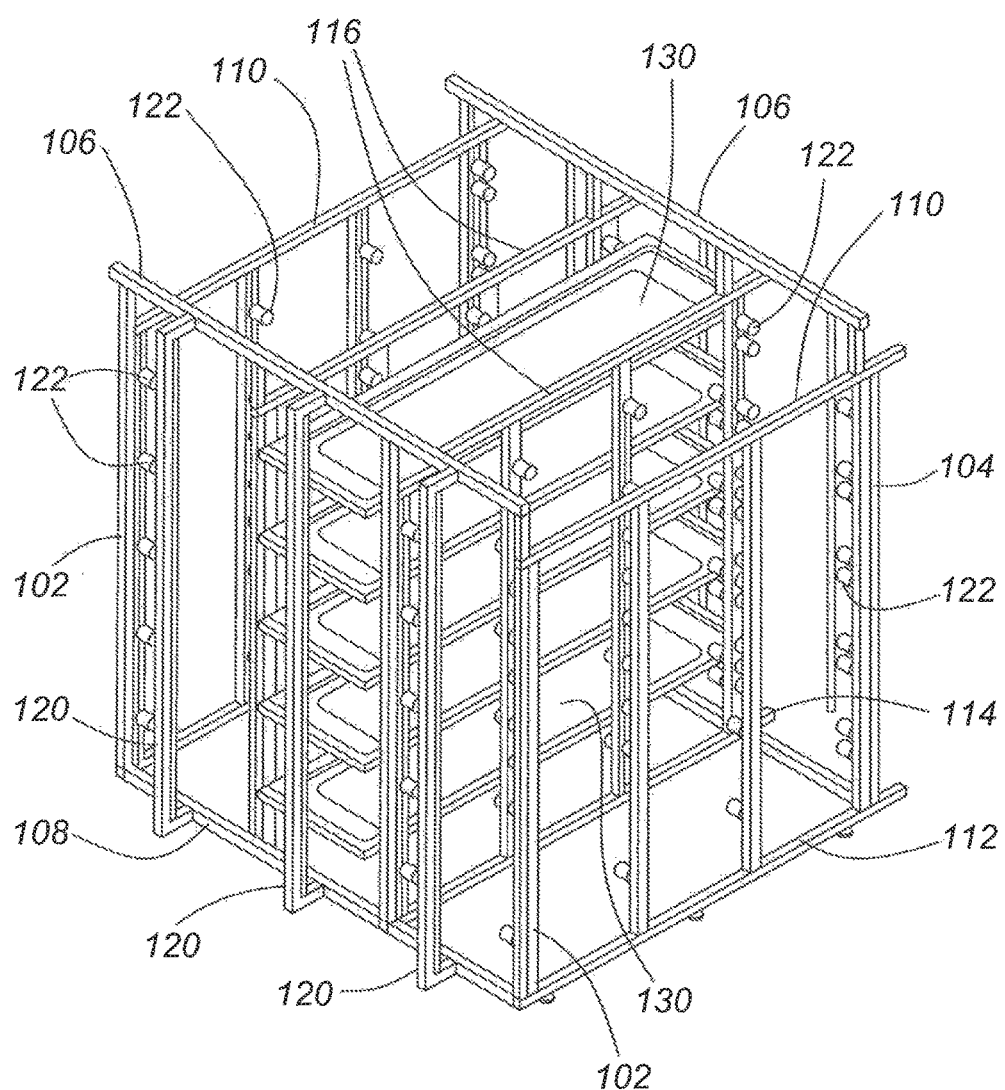
FIG. 6 is an isometric view of one embodiment of a rack unit for use in connection with the mobile storage system of FIG. 1.
Figure 8A:
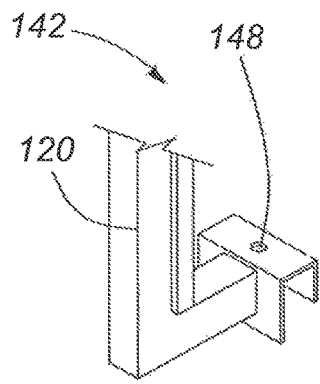
FIGS. 8A to 8C are close-up isometric views of another embodiment of a retention bracket hook arrangement for use in connection with a rack unit of the mobile storage system of FIG. 1.
Figure 8B:
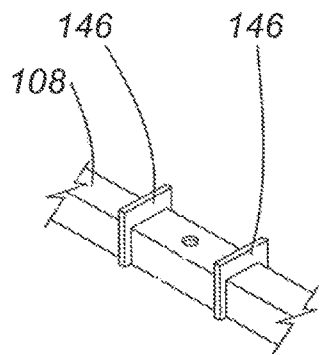
Figure 8C:
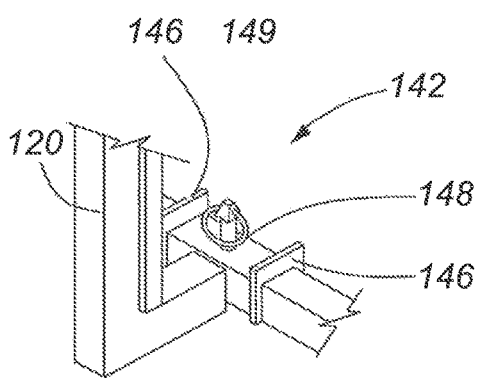

With specific reference to FIGS. 5 and 6, it can be seen that the rack system 100 is coordinated to receive a tray 130 that can hold a cadaver or human remains. In these embodiments, it can be seen that the tray is sized such that it fits comfortably between the laterally adjacent vertical support members. Moreover, it is contemplated that tray 130 can have a laterally extending handle 132 positioned at either or both ends of tray 130, as required by the specific needs of the particular end user application.

Tray support element 122 releasably attaches to the front upper lateral member 106 and front lower lateral member 108. Moreover, tray support element 122 abuts or nearly abuts one end of tray 130 in order to secure tray 130 when in a stowed position within rack unit 100. In this embodiment, it can be seen that rack unit 100 can accommodate fifteen trays (in three rows of five vertically stacked trays) however other arrangements are certainly contemplated as discussed in further detail herein.

Turning to FIGS. 7A to 7C and 8A to 8C, at least one embodiment of tray securing element 120 is illustrated. Tray securing element 120 has a first end 140 and a second end 142. In this embodiment, first end 140 has a bracket retention hook 144 that is adapted to releasably but firmly grip front upper lateral member 106 (which in this embodiment is a square tube, although other cross-sectional shapes are also contemplated). Moreover, a pair of guide plates 146 can be provided which guide bracket retention hook 144 to the proper position and also prevent lateral slippage along front upper lateral member 106.

Similarly, in this embodiment second end 142 has a bracket retention hook 148 that is adapted to releasably but firmly grip front lower lateral member 106 (which in this embodiment is a square tube, although other cross-sectional shapes are also contemplated). Moreover, a pair of guide plates 146 can be provided which guide bracket retention hook 148 to the proper position and prevent lateral slippage along front lower lateral member 106. A wing nut 149 or other suitable mechanical fastener may be provided to secure tray securing element 120 relative to front lower lateral member 106.

Figure 9:
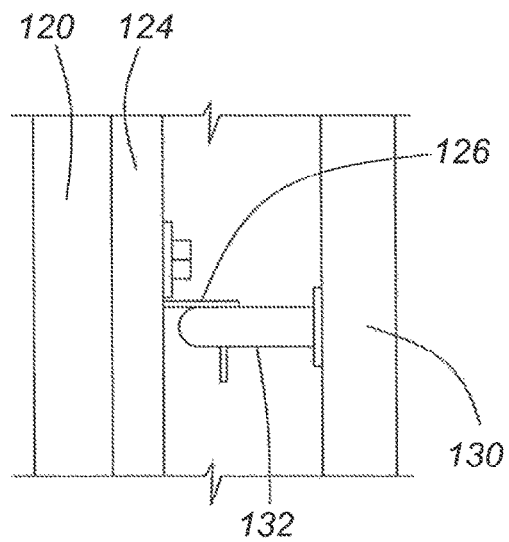
FIG. 9 is a close-up side view of a tray retaining hook for use in connection with a rack unit of the mobile storage system of FIG. 1.

Turning to FIG. 9, a side view of at least one embodiment of tray securing element 120 is illustrated. In this embodiment, tray 130 has a laterally extending handle 132. Further, tray securing element 120 has a tray retaining hook 126 that is mounted on an inner surface 124 of the tray securing element 120. Tray retaining hook 126 engages laterally extending handle 132 when tray securing element 120 is secured in position. In this way and as will be understood by the skilled person, tray 130 is effectively restrained from movement when tray securing element 120 is secured in position and tray retaining hook 126 engages laterally extending handle 132.

Figure 10A:
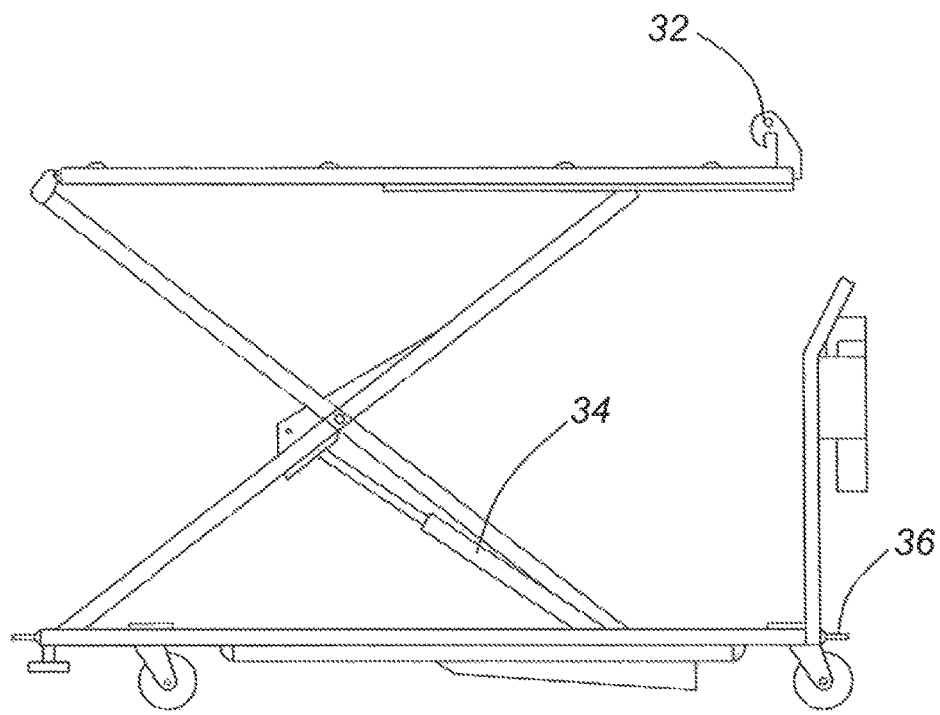
FIG. 10A is a side view of one embodiment of a stretcher for use in connection with the mobile storage system of FIG. 1.
Figure 10B:
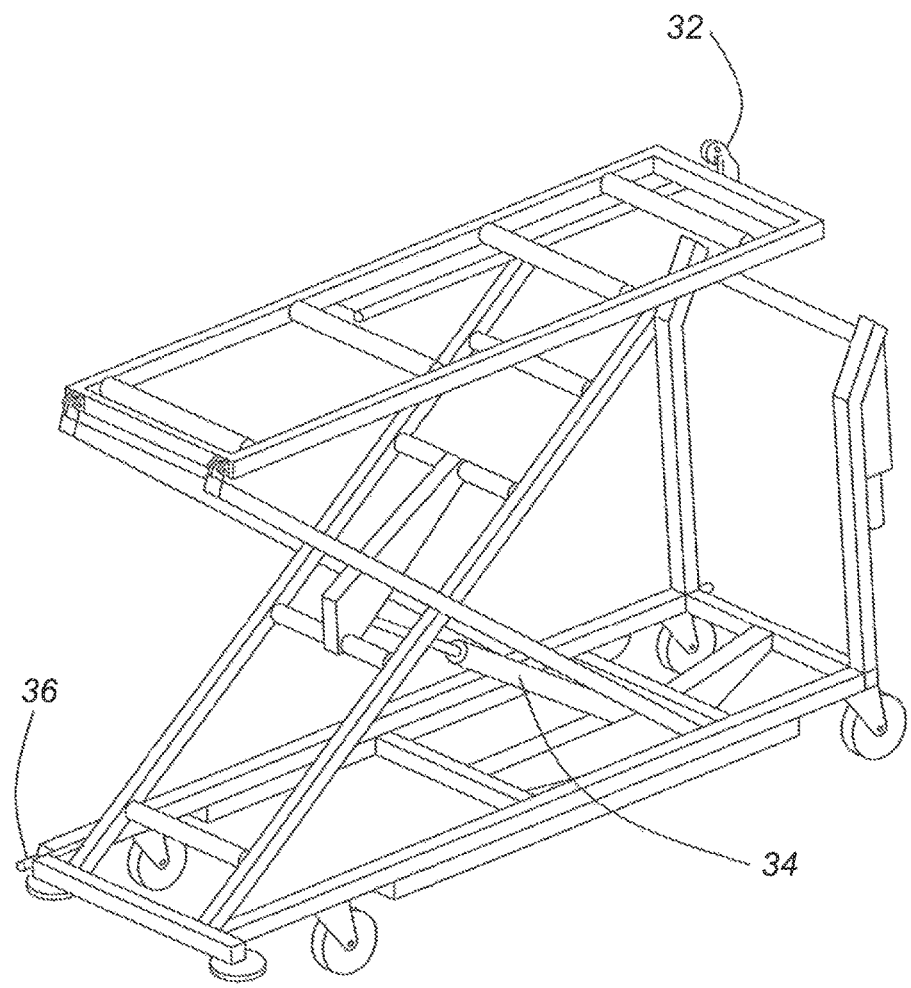
FIG. 10B is an isometric view of one embodiment of a stretcher for use in connection with the mobile storage system of FIG. 1.

Turning to FIGS. 10A and 10B, one embodiment of a stretcher 30 for use in connection with the present invention is illustrated. In this embodiment stretcher 30 has a tray retaining hook 32 for securely yet releasably gripping tray 130. Moreover, stretcher 30 is wheeled and has a height adjustment mechanism 34 for adjusting the stretcher from a first height to at least a second height. A securing point 36 may also be included for securing stretcher 30 when the entire system is in transit.

In this way, a number of trays can be securely stored in the rack units 100 which are in turn secured within the container 12, which allows for entry and egress by way of an access opening 22. Stretcher 30 can be used to transport a cadaver or human remains from a disaster site into the present mobile storage system 10, which can be secured for transit such that the very sensitive contents can be transported and housed in a secure, temperature-controlled, dignified and hygienic manner, all while providing a secure working space for the attending first responders.

The present disclosure provides for reference to specific examples. It will be understood that the examples are intended to describe embodiments of the invention and are not intended to limit the invention in any way. Moreover, it is obvious that the foregoing embodiments of the invention are examples and can be varied in many ways. Such present or future variations are not to be regarded as a departure from the spirit and scope of the invention, and all such modifications as would be obvious to one skilled in the art are intended to be included within the scope of the following claims.

I claim:
1. A mobile storage system comprising:
a container, the container comprising:
    a first end having an internal supporting rear wall, a second end having an internal supporting rear wall, a first longitudinally extending side extending between the first end and the second end and having an internal supporting side wall, a second longitudinally extending side extending between the first end and the second end and having an internal supporting side wall, a supporting floor extending between the first end and the second end, a ceiling extending between the first end and the second end;
    the first end, the second end, the first longitudinally extending side, the second longitudinally extending side, the ceiling and the supporting floor defining a rectangular prismatic cavity;
    at least one of the first longitudinally extending side and the second longitudinally extending side having an access door that corresponds with an access opening, the access door and the access opening positioned between the first end and the second end of the container, and
    a climate control unit for managing the climate within the container; and
    at least one rack unit secured within the rectangular prismatic cavity in at least one of the first end and the second end of the container, the at least one rack unit adapted to receive and securely store at least one tray in a stowed position;
    wherein the at least one rack unit further comprises:
    a front vertical first side support member having a first end and a second end and an inner surface and a front vertical second side support member having a first end and a second end and an inner surface, each of the front vertical first side support member and the front vertical second side support member having at least one tray support element positioned between the respective first end and the second end on the inner surface of the front vertical first side support member and the front vertical second side support member;
    a front upper lateral member having a first end and a second end and levelly extending between the front vertical first side support member and the front vertical second side support member adjacent the respective first end of each of the front vertical first side support member and the front vertical second side support member;
a front lower lateral member having a first end and a second end and levelly extending between the front vertical first side support member and the front vertical second side support member adjacent the respective second end of each of the front vertical first side support member and the front vertical second side support member;
a rear vertical first side support member having a first end and a second end and an inner surface and a rear vertical second side support member having a first end and a second end and an inner surface; each of the rear vertical first side support member and the rear vertical second side support member having at least one tray support element positioned between the respective first end and the second end on the inner surface of the rear vertical first side support member and the rear vertical second side support member;
a rear upper lateral member having a first end and a second end and levelly extending between the rear vertical first side support member and the rear vertical second side support member adjacent the respective first end of each of the rear vertical first side support member and the rear vertical second side support member;
a rear lower lateral member having a first end and a second end and levelly extending between the rear vertical first side support member and the rear vertical second side support member adjacent the respective second end of each of the rear vertical first side support member and the rear vertical second side support member;
the at least one tray having a first end, a second end, a first side and a second side, each of the at least one tray slidably supported by at least one corresponding one of the at least one tray support element in the stowed position, and
at least one vertical tray securing member having a first end and a second end, each at least one vertical tray securing member corresponding to at least one of the at least one tray;
the at least one tray securing member abutting or nearly abutting the first end of the tray in the stowed position, the first end of the at least one vertical tray securing member removably engaging the front upper lateral member and the second end of the at least one vertical tray securing member removably engaging the front lower lateral member.

2. The mobile storage system of claim 1 further comprising a mobile stretcher, the mobile stretcher adjustable from a first height to a least a second height and adapted to securely yet releasably receive the at least one tray, the at least a second height aligning with the at least one tray when it is received in the at least one rack unit.

3. The mobile storage system of claim 1 wherein at least one of the first end and the second end of the front upper lateral support member, the front lower lateral support member, the rear upper lateral support member and the rear lower lateral support member is secured to the internal supporting side wall.

4. The mobile storage system of claim 1 wherein at least one rack unit further comprises an upper first side horizontal member having a first end and a second end and an upper second side horizontal member having a first end and a second end, the upper first side horizontal member extending between adjacent the second end of the front vertical first side support member and adjacent the second end of the rear vertical first side support member, the upper second side horizontal member extending between adjacent the second end of the front vertical second side support member and adjacent the second end of the rear vertical second side support member; and
a lower first side horizontal member having a first end and a second end and a lower second side horizontal member having a first end and a second end, the lower first side horizontal member extending between adjacent the first end of the front vertical first side support member and adjacent the first end of the rear vertical first side support member, the lower second side horizontal member extending between adjacent the first end of the front vertical second side support member and adjacent the first end of the rear vertical second side support member.

5. The mobile storage system of claim 4 wherein at least one of the first end and the second end of one of at least one of the upper first side horizontal member and the upper second side horizontal member is fixed to the internal supporting rear wall.

6. The mobile storage system of claim 4 wherein at least one of the lower first side member and the lower second side member is fixed to the supporting floor.

7. The mobile storage system of claim 4 wherein the at least one rack unit further comprises at least one vertical first side intermediary support member extending between the upper first side horizontal member and the lower first side horizontal member and at least one vertical second side intermediary support member extending between the upper second side horizontal member and the lower second side horizontal member, each of the at least one vertical first side intermediary support member and the at least one vertical second side intermediary support member having an inner surface, each inner surface having at least one tray support element, each at least one tray support element correspondingly engaging and supporting a corresponding one of the at least one tray in the stowed position.

8. The mobile storage system of claim 1 wherein at least one of the first end and the second end of the at least one tray comprises a laterally extending handle.

9. The mobile storage system of claim 8 wherein at least one of the first end and the second end of the at least one vertical tray securing member further comprises a retention bracket hook, the retention bracket hook adapted to snugly yet releasably engage from at least one of the first upper lateral member and the first lower lateral member.

10. The mobile storage system of claim 9 wherein the at least one vertical tray securing member further comprises a tray retaining hook positioned between the first end and the second end of the at least one vertical tray securing member, the tray retaining hook adapted to engage the laterally extending handle of the at least one tray.

11. The mobile storage system of claim 1 wherein the rack unit further comprises at least one vertically oriented bump stopper abutting the at least one of the first end and the second end of the at least one tray in the stowed position, the at least one vertically oriented bump stopper secured to the internal supporting rear wall.

12. The mobile storage system of claim 1 wherein the rack unit further comprises at least one front vertical intermediary support member having a first end and a second end, each at least one front vertical intermediary support member extending vertically between a front upper lateral member and the front lower lateral member, each at least one front vertical intermediary support member positioned between the first end of the front upper lateral member and the front lower lateral member and the second end of the front upper lateral member and the front lower lateral member;

at least one rear vertical intermediary support member having a first end and a second end, each at least one rear vertical intermediary support member extending vertically between the rear upper lateral member and the rear lower lateral member, each at least one rear vertical intermediary support member positioned between the first end of the rear upper lateral member and the rear lower lateral member and the second end of the rear upper lateral member and the rear lower lateral member; and each of the at least one front vertical intermediary support member and the at least one rear vertical intermediary support member having a first side surface and a second side surface, each first side surface and second side surface having at least one tray support element, wherein the at least one tray is a plurality of trays, each of the plurality of trays is slidably supported by a corresponding at least one tray support element in the stowed position.

13. The mobile storage system of claim 12 wherein the rack unit further comprises at least one upper intermediary horizontal member corresponding to the at least one front vertical intermediary support member and the at least one rear vertical intermediary support member, the at least one upper intermediary horizontal member having a first end and a second end, the at least one upper intermediary horizontal member extending between adjacent the second end of at least one front vertical intermediary support member and adjacent the second end of the at least one rear vertical intermediary support member; and at least one lower intermediary horizontal member corresponding to the at least one front vertical intermediary support member and the at least one rear vertical intermediary support member, the at least one lower intermediary horizontal member having a first end and a second end, the at least one lower intermediary horizontal member extending between adjacent the first end of at least one front vertical intermediary support member and adjacent the first end of the at least one rear vertical intermediary support member.

14. The mobile storage system of claim 13 wherein at least one of the first end and the second end of at least one upper intermediary horizontal member is fixed to the internal supporting rear wall.

15. The mobile storage system of claim 13 wherein the at least one lower intermediary horizontal member is fixed to the supporting floor.

16. The mobile storage system of claim 13 wherein the rack unit further comprises at least one vertical intermediary support member extending between the at least one upper intermediary horizontal member and the at least one lower intermediary horizontal member, the at least one vertical intermediary support member having a first side surface and a second side surface, each first side surface and second side surface having at least one tray support element, each at least one tray support element correspondingly engaging and supporting a corresponding one of the at least one tray in the stowed position.

17. The mobile storage system of claim 1 wherein the at least one tray support element is a rolling support element.

18. The mobile storage system of claim 1 wherein the container further comprises a lighting unit positioned on the ceiling.

19. The mobile storage system of claim 1 further comprising a work surface mounted to one of inner supporting side walls of the container.

* * * * *